United States Patent
Li et al.

(10) Patent No.: US 9,809,834 B2
(45) Date of Patent: Nov. 7, 2017

(54) PROCESSES OF TREATING CELLULOSIC MATERIAL

(71) Applicants: NOVOZYMES A/S, Bagsvaerd (DK); NOVOZYMES NORTH AMERICA, INC., Franklinton, NC (US)

(72) Inventors: Xin Li, Raleigh, NC (US); Mads Torry Smith, Raleigh, NC (US); Brandon Emme, Kansas City, MO (US); Lorraine Putnam, Youngsville, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/402,897

(22) PCT Filed: May 29, 2013

(86) PCT No.: PCT/US2013/043084
§ 371 (c)(1),
(2) Date: Nov. 21, 2014

(87) PCT Pub. No.: WO2013/181233
PCT Pub. Date: Dec. 5, 2013

(65) Prior Publication Data
US 2015/0176043 A1 Jun. 25, 2015

Related U.S. Application Data

(60) Provisional application No. 61/652,559, filed on May 29, 2012.

(51) Int. Cl.
| | | |
|---|---|---|
| C12P 19/14 | (2006.01) | |
| C12P 19/02 | (2006.01) | |
| C13K 1/02 | (2006.01) | |
| C13K 13/00 | (2006.01) | |

(52) U.S. Cl.
CPC .............. *C12P 19/14* (2013.01); *C12P 19/02* (2013.01); *C12Y 110/03002* (2013.01); *C13K 1/02* (2013.01); *C13K 13/002* (2013.01); *C12P 2201/00* (2013.01); *C12P 2203/00* (2013.01)

(58) Field of Classification Search
None
See application file for complete search history.

(56) References Cited

U.S. PATENT DOCUMENTS

| | | |
|---|---|---|
| 2008/0138872 A1 | 6/2008 | Smith et al. |
| 2010/0221805 A1 | 9/2010 | Kelly |
| 2011/0008863 A1 | 1/2011 | Zhu et al. |
| 2011/0171685 A1 | 7/2011 | Li et al. |
| 2013/0017586 A1 | 1/2013 | Ropars et al. |

FOREIGN PATENT DOCUMENTS

WO  2008/134259 A1  11/2008

OTHER PUBLICATIONS

Lenartovicz V et al. Temperature and carbon source affect the production and secretion of a thermostable beta-xylosidase by Aspergillus fumigatus. 2003. Process Biochemistry. 38:1775-1780.*

* cited by examiner

*Primary Examiner* — Paul Holland
(74) *Attorney, Agent, or Firm* — Kelly Reynolds

(57) ABSTRACT

The invention relates to processes of producing sugars and/or fermentation products from pretreated cellulosic material comprising the steps of: preconditioning pretreated cellulosic material; hydrolyzing using a cellulolytic enzyme preparation; and fermenting sugars with a microorganism; wherein a solid-liquid separation step, resulting in a solid fraction and a liquid fraction, is carried out: after preconditioning, but before hydrolysis; or after hydrolysis, but before fermentation; wherein phenol oxidizing enzyme and hemicellulase are present or added during preconditioning; after preconditioning, but before hydrolysis; or during hydrolysis.

17 Claims, No Drawings

PROCESSES OF TREATING CELLULOSIC MATERIAL

CROSS-REFERENCE TO RELATED APPLICATIONS

This application is a 35 U.S.C. 371 national application of PCT/US2013/043084 filed May 29, 2013 and published on Dec. 5, 2013 as WO2013/181233, which claims priority or the benefit under 35 U.S.C. 119 of U.S. provisional application No. 61/652,559 filed May 29, 2012, the contents of which are fully incorporated herein by reference.

FIELD OF THE INVENTION

The invention relates to processes of producing sugars and/or fermentation products from pretreated cellulosic materials wherein improved solid-liquid separation is obtained.

BACKGROUND OF THE INVENTION

Cellulosic material provides an attractive platform for generating alternative energy sources to fossil fuels. The conversion of cellulosic material (e.g., from lignocellulosic feedstock) into biofuels has the advantages of the ready availability of large amounts of feedstock, the desirability of avoiding burning or land filling the materials, and the cleanliness of the biofuels (such as ethanol). Once the cellulosic material is converted to fermentable sugars, e.g., glucose, the fermentable sugars may be fermented by yeast into biofuels, such as ethanol.

Before or after hydrolysis pretreated cellulosic material may be subjected to solid-liquid separation. The efficiency of the solid-liquid separation is important for the final MESP (Minimum Ethanol Sales Price). High solid-liquid separation results in a lower MESP. Therefore, it would be an advantage in the art to improve the solid-liquid separation in methods and processes of producing sugars and/or fermentation products from pretreated cellulosic material.

SUMMARY OF THE INVENTION

Described herein are processes of improving solid-liquid separation in processes of producing sugars and/or fermentation products from pretreated cellulosic material.

In the first aspect the invention relates to processes of producing a fermentation product from a pretreated cellulosic material, comprising the steps of:
  i) preconditioning a pretreated cellulosic material;
  ii) hydrolyzing the pretreated cellulosic material using a cellulolytic enzyme preparation;
  iii) fermenting sugars with a microorganism;
wherein a solid-liquid separation step, resulting in a solid fraction and a liquid fraction, is carried out:
  a) after preconditioning, but before hydrolysis; or
  b) after hydrolysis, but before fermentation;
wherein a phenol oxidizing enzyme and/or a hemicellulase are present or added:
  during preconditioning; or
  after preconditioning, but before hydrolysis; or
  during hydrolysis.

In a preferred embodiment the pretreated cellulosic material is dilute acid pretreated cellulosic material. In another embodiment the pretreated cellulosic material is autohydrolyzed pretreated cellulosic material.

In a preferred embodiment the phenol oxidizing enzyme is a laccase (e.g., from *Myceliophthora thermophila*). In a preferred embodiment the hemicellulase is a xylanase (e.g., derived from *Aspergillus aculeatus* or *Aspergillus fumigatus* and/or a beta-xylosidase (e.g., derived from *Aspergillus fumigatus*).

The hemicellulase(s) may also be part of a cellulolytic enzyme preparation comprising one or more hemicellulases, such as xylanase and/or beta-xylosidase. In an embodiment the cellulolytic enzyme preparation is derived from *Trichoderma* (e.g., *Trichoderma reesei*). The cellulolytic enzyme preparation generally includes endoglucanase (EG), cellobiohydrolase (CBH), and beta-glucosidase (BG). The cellulolytic enzyme preparation may further contain a polypeptide having cellulolytic enhancing activity (e.g., *Thermoascus aurantiacus* or *Penicillium emersonii* cellulolytic enhancing polypeptide), beta-glucosidase (e.g., *Aspergillus fumigatus* or *Aspergillus oryzae* beta-glucosidase) and/or hemicellulase.

In another aspect the invention relates to processes of producing sugars from pretreated cellulosic material comprising the steps of:
  (a) preconditioning a pretreated cellulosic material;
  (b) hydrolyzing the pretreated cellulosic material using a cellulolytic enzyme preparation;
wherein a solid-liquid separation step, resulting in a solid fraction and a liquid fraction, is carried out:
  i) after preconditioning, but before hydrolysis; or
  ii) after hydrolysis;
wherein a phenol oxidizing enzyme and/or a hemicellulase are present or added:
  a. during preconditioning; or
  b. after preconditioning, but before hydrolysis;
  c. during hydrolysis.

The enzyme used may be the same as used in a process of producing fermentation products of the invention. The sugars produced according to the invention may be converted into a number of products including fermentation products (e.g., ethanol or butanol) or into syrups (e.g., High Fructose Corn Syrups) and plastics including polyethylene, polystyrene, polypropylene). Other contemplated end products include lactic acid which can serve as a feedstock for production of polylactic acid (PLA) to replace petrochemical packaging materials such as PET.

Hemicellulose: As used herein, the term "hemicellulose" refers to an oligosaccharide or polysaccharide of biomass material other than cellulose. Hemicellulose is chemically heterogeneous and includes a variety of polymerized sugars, primarily D-pentose sugars, such as xylans, xyloglucans, arabinoxylans, and mannans, in complex heterogeneous branched and linear polysaccharides or oligosaccharides that are bound via hydrogen bonds to the cellulose microfibrils in the plant cell wall, and wherein xylose sugars are usually in the largest amount. Hemicelluloses may be covalently attached to lignin, and usually hydrogen bonded to cellulose, as well as to other hemicelluloses, which help stabilize the cell wall matrix forming a highly complex structure. Hemicellulosic material includes any form of hemicellulose, such as polysaccharides degraded or hydrolyzed to oligosaccharides. It is understood herein that the hemicellulose may be in the form of a component of lignocellulose, a plant cell wall material containing lignin, cellulose, and hemicellulose in a mixed matrix.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. The mature polypeptide can be predicted using the SignalP program (Nielsen et al., 1997, *Protein Engineering* 10: 1-6).

Mature polypeptide coding sequence: The term "mature polypeptide coding sequence" is defined herein as a nucleotide sequence that encodes a mature polypeptide having biological activity. The mature polypeptide coding sequence can be predicted using the SignalP program (Nielsen et al., 1997, supra).

Pretreated corn stover: The term "PCS" or "Pretreated Corn Stover" means a cellulosic material derived from corn stover that has been pretreated (e.g., by treatment with heat and dilute sulfuric acid).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment−Total Number of Gaps in Alignment)

Solid-Liquid Separation: Solid-liquid separation may be achieved in any way, including using a screw press, centrifugation, belt press, drum filter, hydrocyclone and/or filter press, or any kind of apparatus which can handle solid/liquid separation, including gravity-fed systems or apparatuses.

Variant: The term "variant" means a polypeptide (e.g., enzyme) comprising an alteration, i.e., a substitution, insertion, and/or deletion of one or more (e.g., several) amino acid residues at one or more positions. A substitution means a replacement of the amino acid occupying a position with a different amino acid; a deletion means removal of the amino acid occupying a position; and an insertion means adding an amino acid adjacent to the amino acid occupying a position.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION

The present invention relates to processes of producing sugars and/or fermentation products from pretreated cellulosic material comprising a solid-liquid separation step. According to the invention the separation of pretreated cellulosic material into a solid fraction and a liquid fraction is improved compared to the same process where no enzymes are added.

The inventors found that when subjecting pretreated lignocellulosic materials to a laccase and a hemicellulase either during preconditioning; or after preconditioning, but before hydrolysis; or during hydrolysis, an improved solid-liquid separation is obtained.

In the first aspect the invention relates to process of producing fermentation products, such as especially ethanol, from pretreated cellulosic material, comprising the steps of:
(a) preconditioning a pretreated cellulosic material;
(b) hydrolyzing the pretreated cellulosic material using a cellulolytic enzyme preparation;
(c) fermenting sugars with a microorganism;
wherein a solid-liquid separation step, resulting in a solid fraction and a liquid fraction, is carried out:
(i) after preconditioning, but before hydrolysis; or
(ii) after hydrolysis, but before fermentation;
wherein a phenol oxidizing enzyme and/or a hemicellulase are present or added:
during preconditioning; or
after preconditioning, but before hydrolysis; or
during hydrolysis.

In a preferred embodiment the pretreated cellulosic material is dilute acid pretreated cellulosic material. In another embodiment the pretreated cellulosic material is autohydrolyzed pretreated cellulosic material.

The phenol oxidizing enzyme may be any phenol oxidizing enzyme. In a preferred embodiment the phenol oxidizing enzyme is a laccase. Specifically contemplated is the *Myceliophthora thermophila* laccase (disclosed in WO 95/33836 (Novozymes). Other suitable laccases are mentioned in the "Laccases"-section below.

Other phenol oxidizing enzymes may also be used. Examples are given below in the "Phenol Oxidizing Enzymes"-section.

The hemicellulase may be any hemicellulase (e.g., of fungal or bacterial origin). In a preferred embodiment the hemicellulase is xylanase and/or xylosidase. Specifically the hemicellulase may be a xylanase, (e.g., GH10 xylanase) derived from *Aspergillus aculeatus* (e.g., Xyl II disclosed in WO 94/21785) or *Aspergillus fumigatus* (e.g., one disclosed in WO 2006/078256) and/or a beta-xylosidase derived from *Aspergillus fumigatus* (e.g., one disclosed in WO 2011/057140).

Other suitable hemicellulases are listed in the "Hemicellulases"-section below.

In an embodiment the hemicellulase is a constituent in a cellulolytic enzyme preparation.

In such embodiment the hemicellulase may be a cellulolytic enzyme preparation (e.g., from *Trichoderma reesei*) further comprising a foreign hemicellulase (i.e., not derived from the organism producing the cellulolytic enzyme preparation), such as a xylanase (e.g., *Aspergillus aculateus* or *Aspergillus fumigatus* xylanase) and/or xylosidase (e.g., *Aspergillus fumigatus* beta-xylosidase).

The pretreated cellulosic material may be pretreated using any suitable method. Suitable pretreatment methods are listed in the "Pretreatment"-section below. In a preferred embodiment the material is dilute acid pretreated or auto-hydrolyzed.

In an embodiment the pretreated cellulosic material is unwashed and/or un-detoxified.

In an embodiment the pretreated material is squeezed cellulosic material.

According to the invention the cellulosic material may be unwashed pretreated corn stover (PCS), unwashed pretreated corn cob, unwashed pretreated wheat straw, unwashed pretreated rice straw or unwashed pretreated switch grass. In a preferred embodiment the cellulosic material is unwashed dilute acid pretreated corn stover.

Other examples of contemplated cellulosic material can be found in the "Cellulosic Materials"-section below.

According to the invention hydrolysis may be carried out at 5-50% (w/w) TS, such as 10-40 (w/w) % TS, 15-35 (w/w) % TS, and 20-30 (w/w) % TS. The cellulosic material may be in a preferred embodiment be pretreated unwashed corn stover (PCS), corn cob, wheat straw, rice straw and switch grass.

In an embodiment preconditioning occurs at 5-50 (w/w) % TS, such as 10-40 (w/w) % TS, such as 15-35 (w/w) % TS, such as 20-30 (w/w) % TS.

In an embodiment preconditioning of the cellulosic material occurs for at least 30 minutes, e.g., at least 1 hour, 2 hours, 4 hours, 8 hours, 12 hours, or 24 hours, or longer, or from 30 minutes to 24 hours.

In an embodiment preconditioning of the cellulosic material occurs at a temperature between 20-70° C., such as between 40 and 60° C.

In an embodiment the phenol oxidizing enzyme loading, especially laccase, is between 1-500 micrograms Enzyme Protein (EP)/g cellulose, such as 5-100 micrograms EP/g cellulose.

In an embodiment the hemicellulase loading is between 0.01 and 20 mg EP/g cellulose, such as 0.1-1 mg EP/g cellulose.

Cellulosic Materials

As used herein, the term "cellulosic material" refers to any lignocellulosic material containing cellulose (a chemically homogeneous oligosaccharide or polysaccharide of beta-(1-4)-D-glucan (polymer containing beta (1-4) linked D-glucose units)). Although generally polymorphous, cellulose can be found in plant tissue primarily as an insoluble crystalline matrix of parallel glucan chains. Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, Bioresource Technology 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, N.Y.). Cellulosic material includes any form of cellulose, such as polysaccharides degraded or hydrolyzed to oligosaccharides. It is understood herein that the cellulose may be in the form of a component of lignocellulose, a plant cell wall material containing lignin, cellulose, and hemicellulose in a mixed matrix.

In one aspect, the cellulosic material is herbaceous material (including energy crops). In another aspect, the cellulosic material is agricultural residue. In another aspect, the cellulosic material is wood (including forestry residue). In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is wheat straw. In another aspect, the cellulosic material is bagasse. In another aspect, the cellulosic material is corn cob. In another aspect, the cellulosic material is switchgrass. In another aspect, the cellulosic material is corn fiber. In another aspect, the cellulosic material is rice straw. In another aspect, the cellulosic material is miscanthus. In another aspect, the cellulosic material is arundo. In another aspect, the cellulosic material is bamboo. In another aspect, the cellulosic material is orange peel. In another aspect, the cellulosic material is poplar. In another aspect, the cellulosic material is pine. In another aspect, the cellulosic material is aspen. In another aspect, the cellulosic material is fir. In another aspect, the cellulosic material is spuce. In another aspect, the cellulosic material is willow. In another aspect, the cellulosic material is eucalyptus.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

In another aspect, the cellulosic material is an aquatic biomass. As used herein the term "aquatic biomass" means biomass produced in an aquatic environment by a photosynthesis process. The aquatic biomass can be algae; submerged plants; emergent plants; and floating-leaf plants.

Processes of the Invention

Processes of the invention produce sugars and/or fermentation products from pretreated cellulosic material. The pre-treatment may be any pre-treatment. Examples of suitable pre-treatment can be found in the "Pretreatment" section below. Processes of the invention generally include a step of preconditioning the pretreated cellulosic material; hydrolyzing the preconditioned material preferably using a cellulolytic enzyme preparation; fermenting resulting sugars with a microorganism. Processes of the invention include a solid-liquid separation step resulting in a solid fraction and a liquid fraction.

According to the invention hydrolysis may be carried out at 10-40% TS, such as 15-35% TS, such as 20-30% TS. The cellulosic material may be in a preferred embodiment be pretreated unwashed corn stover (PCS), corn cob, wheat straw, rice straw and switch grass.

In an embodiment the solid-liquid separation is step is carried out after preconditioning, but before hydrolysis.

In an embodiment of the invention pretreated cellulosic material is dilute acid pretreated cellulosic material or a similar kind of pretreated material, where the $C_5$ sugars end up in the liquid fraction resulting from solid-liquid separation. In an embodiment the solid fraction resulting from the solid-liquid separation step, is hydrolyzed and then fermented. The liquid fraction resulting from the solid-liquid separation step, may also be fermented. In an embodiment the fermentation products from the solid fraction and/or the liquid fraction fermentation(s) is/are, optionally recovered. In an embodiment the liquid fraction is detoxified after solid-liquid separation. In an embodiment the detoxified liquid fraction is hydrolyzed together with the solid fraction and then fermented (i.e., together with the hydrolyzed solid fraction). In an embodiment the solid fraction resulting from the solid-liquid separation step, is hydrolyzed and then fermented together with the liquid fraction resulting from the solid-liquid separation step.

In an embodiment the solid-liquid separation is carried out after hydrolysis, but before fermentation. In such embodiment the liquid fraction resulting from the solid-liquid separation step, may be fermented and optionally recovered. The solid fraction does not contain a significant amount of sugars.

In an embodiment the pretreated cellulosic material is auto-hydrolyzed pretreated cellulosic material or similar, where the $C_5$ sugars end up in the solid fraction. In an embodiment the solid-liquid separation is carried out after preconditioning, but before hydrolysis. In an embodiment the solid fraction resulting from solid-liquid separation, is hydrolyzed and then fermented. The liquid fraction resulting from the solid-liquid separation, may be reused as water in, e.g., fermentation.

In an embodiment the solid-liquid separation is carried out after hydrolysis, but before fermentation. In an embodiment the solid fraction resulting from the solid liquid separation, is fermented and optional recovered.

In an embodiment the process of producing a fermentation product from pretreated cellulosic material of the invention comprising the steps of:
  preconditioning pretreated cellulosic material;
  solid-liquid separation resulting in a solid fraction and a liquid fraction;
  hydrolyzing the solid fraction using a cellulolytic enzyme preparation;
  fermenting sugars from the hydrolyzed solid fraction, and/or optionally the liquid fraction, with a microorganism;
wherein a phenol oxidizing enzyme and/or a hemicellulase are present or added:
  during preconditioning; or
  after preconditioning, but before hydrolysis;
  during hydrolysis.

In an embodiment of the process of the invention, the pretreated cellulosic material is dilute acid pretreated cellulosic material. In an embodiment the fermented material is recovered, e.g., by distillation.

In another embodiment of the invention, the pretreated cellulosic material is auto-hydrolyzed acid pretreated cellulosic material. In an embodiment the solid fraction resulting from the solid-liquid separation is hydrolyzed and then fermented. In an embodiment the liquid fraction resulting from the solid-liquid separation is reused as water in fermentation. In an embodiment the fermented material is recovered, e.g., by distillation.

In an embodiment the invention relates to processes of producing fermentation products from pretreated cellulosic material comprising the steps of:
  preconditioning a pretreated cellulosic material;
  hydrolyzing the pretreated cellulosic material using a cellulolytic enzyme preparation;
  solid-liquid separation;
  fermenting the sugars from the liquid fraction with a microorganism;
wherein a phenol oxidizing enzyme and/or a hemicellulase are present or added:
  during preconditioning; or
  after preconditioning, but before hydrolysis;
  during hydrolysis.

In an embodiment the pretreated cellulosic material is dilute acid pretreated cellulosic material.

In an embodiment the fermented material is recovered, e.g., by distillation.

In an embodiment the invention relates to processes of producing fermentation products from pretreated cellulosic material comprising the steps of:
  preconditioning a pretreated cellulosic material;
  hydrolyzing the pretreated cellulosic material using a cellulolytic enzyme preparation;
  solid-liquid separation;
  fermenting the sugars from the solid fraction with a microorganism;
wherein a phenol oxidizing enzyme and/or a hemicellulase are present or added:
  during preconditioning; or
  after preconditioning, but before hydrolysis;
  during hydrolysis.

In an embodiment the pretreated cellulosic material is auto-hydrolyzed pretreated cellulosic material. In an embodiment the fermented material is recovered, e.g., by distillation.

According to the processes of the invention hydrolysis and fermentation are carried out as separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC).

In a preferred embodiment the fermentation product is an alcohol (e.g., ethanol or butanol), an organic acid, a ketone, an amino acid, or a gas.

A process of the invention results in an improved solid-liquid separation compared to a corresponding process where no phenol oxidizing enzyme and hemicellulase are present or added.

In an aspect of the invention the invention relates to processes of producing sugars from pretreated cellulosic material comprising the steps of:
  a) preconditioning a pretreated cellulosic material;
  b) hydrolyzing the pretreated cellulosic material using a cellulolytic enzyme preparation;
wherein a solid-liquid separation step, resulting in a solid fraction and a liquid fraction, is carried out:
  i) after preconditioning, but before hydrolysis; or
  ii) after hydrolysis;
wherein a phenol oxidizing enzyme and/or a hemicellulase are present or added:
  during preconditioning; or
  after preconditioning, but before hydrolysis;
  during hydrolysis.

The enzyme(s) used may be the same as used in a process of producing fermentation products of the invention. The sugars produced according to the invention may be converted into a number of end products including fermentation products (e.g., ethanol or butanol) or into syrups (e.g., High Fructose Corn Syrups) and plastics including polyethylene, polystyrene, polypropylene). Other contemplated end products include lactic acid which can serve as a feedstock for production of polylactic acid (PLA) to replace petrochemical packaging materials such as PET.

Pretreatment

The starting material used in a process of the invention is pretreated, e.g., by chemical pretreatment, physical pretreatment, or chemical pretreatment and physical pretreatment. Examples of such pretreatments are described below. In one aspect, the pretreated cellulosic material has been pretreated by a chemical pretreatment. In another aspect, the pretreated cellulosic material has been pretreated by physical pretreatment. In another aspect, the pretreated cellulosic material has been pretreated by a chemical pretreatment and a physical pretreatment.

Any suitable pretreatment process known in the art may be used to disrupt plant cell wall components of cellulosic material (see, e.g., Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technol.* 100: 10-18; Mosier et al., 2005, *Bioresource Technol.* 96: 673-686; Taherzadeh and Karimi, 2008, *Int. J. of Mol. Sci.* 9: 1621-1651; Yang and Wyman, 2008, *Biofuels Bioproducts and Biorefining-Biofpr.* 2: 26-40).

The cellulosic material can also be subjected to particle size reduction, pre-soaking, wetting prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments. In a preferred embodiment the cellulosic material (e.g., unwashed corn stover) is dilute acid pretreated.

The cellulosic material is pretreated before preconditioning, hydrolysis (saccharification) and/or fermentation.

Steam Pretreatment: In steam pretreatment, cellulosic material is heated to disrupt the plant cell wall components, including lignin, hemicellulose, and cellulose to make the cellulose and other fractions, e.g., hemicellulose, accessible to enzymes. Cellulosic material is passed to or through a reaction vessel where steam is injected to increase the temperature to the required temperature and pressure and is retained therein for the desired reaction time. Steam pretreatment may be performed at 140-230° C., e.g., 160-200° C., or 170-190° C., where the optimal temperature range depends on any addition of a chemical catalyst. Residence time for the steam pretreatment may be 1-15 minutes, e.g., 3-12 minutes, or 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to hemicellulose monosaccharides and hemicellulose oligosaccharides, which become more solubilized. Lignin is removed to only a limited extent. The resulting liquor primarily contains dissolved hemicellulosic material (e.g., hemicellulose monosaccharides and hemicellulose oligosaccharides), whereas the remaining solids primarily consists of cellulosic material.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* 105-108: 69-85, and Mosier et al., 2005, *Bioresource Technology* 96: 673-686, and U.S. Published Application 2002/0164730.

In one aspect, the chemical pretreatment is carried out as an acid treatment, such as a continuous dilute and/or mild acid treatment. The acid may be sulfuric acid, but other acids can also be used, such as acetic acid, citric acid, nitric acid, phosphoric acid, tartaric acid, succinic acid, hydrogen chloride, or mixtures thereof. Mild and/or dilute acid treatment is conducted in the pH range of preferably 1-5, more preferably 1-4, and most preferably 1-3. In one aspect, the acid concentration is in the range from preferably 0.01 to 20 wt. % acid, more preferably 0.05 to 10 wt. % acid, even more preferably 0.1 to 5 wt. % acid, and most preferably 0.2 to 2.0 wt. % acid. The acid is contacted with cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In one aspect, cellulosic material is present during pretreatment in amounts preferably between 10-80 wt. %, e.g., between 20-70 wt. %, or between 30-60 wt. %, such as around 50 wt. %. The pretreated cellulosic material can be unwashed or washed using any method known in the art, e.g., washed with water.

Autohydrolysis is a commonly used method for pretreatment of cellulosic materials. The cellulosic material is treated with chemical-free and water only media at temperatures from typically 130-230° C.) and pretreatment times from a few seconds to several hours (Capek-Ménard et al., 1987, *Canadian Journal of Chemical Engineering* 65(4): 689-692 and Saska and Ozer, 1995, *Biotechnol. Bioeng.* 45: 517-523. The process causes hemicellulose depolymerization (mainly converted into soluble oligomers as a major reaction product) and lignin transformation due to the high temperature, thus increasing the potential of cellulose hydrolysis (Kabel at al., 2007, *Bioresource Technol.* 98: 2034-2042 and Lee at al., 2009, *Bioresource Technol.* 100: 6434-6441).

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, more preferably about 150 to about 250 psi. In another aspect, high temperature means temperatures in the range of about 100 to about 300° C., preferably about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in an aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from lignocellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

In a preferred embodiment the pretreated cellulosic material is dilute acid pretreated cellulosic material. In another embodiment the pretreated cellulosic material is autohydrolyzed pretreated cellulosic material.

Fermentation

Sugars obtained from hydrolysis (saccharification) of the cellulosic material can be fermented by one or more (several) fermenting microorganisms capable of fermenting the sugars directly or indirectly into a desired fermentation product (e.g., ethanol).

"Fermentation" refers to any fermentation process or any process comprising a fermentation step. Fermentation also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

Sugars released from hydrolysis (saccharification) of preconditioned unwashed pretreated cellulosic material may be fermented to a product, e.g., ethanol, by a fermenting organism, such as yeast. Hydrolysis (saccharification) and fermentation can be separate or simultaneous, or as described below.

Hydrolysis (saccharification) and fermentation, separate or simultaneous, include, but are not limited to, separate hydrolysis (saccharification) and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC). SHF uses separate process steps to first hydrolyze (saccharify) cellulosic material to fermentable sugars, e.g., glucose, cellobiose, cellotriose, and pentose sugars, and then ferment the fermentable sugars to ethanol. In SSF, the enzymatic hydrolysis of cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (several) steps where the same organism is used to produce the enzymes for conversion of the cellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

Fermenting Organisms

"Fermenting organism" refers to any microorganism, including bacterial and fungal organisms, suitable for use in a fermentation process to produce a desired fermentation product. The fermenting organism can be hexose (i.e., $C_6$) and/or pentose ($C_5$) fermenting organisms, or a combination thereof. Both hexose and pentose fermenting organisms are well known in the art. Suitable fermenting organisms are able to ferment, i.e., convert, sugars, such as glucose, xylose, xylulose, arabinose, maltose, mannose, galactose, and/or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_5$ sugars include bacterial and fungal organisms, such as yeast. Preferred $C_5$ fermenting yeast include strains of *Pichia*, preferably *Pichia stipitis*, such as *Pichia stipitis* CBS 5773; strains of *Candida*, preferably *Candida boidinii*, *Candida brassicae*, *Candida diddensii*, *Candida pseudotropicalis*, *Candida sheatae*, or *Candida utilis*.

Other fermenting organisms include strains of *Zymomonas*, such as *Zymomonas mobilis*; *Hansenula*, such as *Hansenula anomala*; *Kluyveromyces*, such as *K. marxianus*, *K. lactis*, *K. thermotolerans*, and *K. fragilis*; *Schizosaccharomyces*, such as *S. pombe*; *E. coli*, especially *E. coli* strains that have been genetically modified to improve the yield of ethanol; *Clostridium*, such as *Clostridium acetobutylicum*, *Chlostridium thermocellum*, and *Chlostridium phytofermentans*; *Geobacillus* sp.; *Thermoanaerobacter*, such as *Thermoanaerobacter saccharolyticum*; and *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Klebsiella*, such as *K. oxytoca*.

In one aspect, the yeast is a *Saccharomyces* spp. In another aspect, the yeast is *Saccharomyces cerevisiae*. In another aspect, the yeast is *Saccharomyces distaticus*. In another aspect, the yeast is *Saccharomyces uvarum*. In another aspect, the yeast is a *Kluyveromyces*. In another aspect, the yeast is *Kluyveromyces marxianus*. In another aspect, the yeast is *Kluyveromyces fragilis*. In another aspect, the yeast is a *Candida*. In another aspect, the yeast is *Candida boidinii*. In another aspect, the yeast is *Candida brassicae*. In another aspect, the yeast is *Candida diddensii*. In another aspect, the yeast is *Candida pseudotropicalis*. In another aspect, the yeast is *Candida utilis*. In another aspect, the yeast is a *Clavispora*. In another aspect, the yeast is *Clavispora lusitaniae*. In another aspect, the yeast is *Clavispora opuntiae*. In another aspect, the yeast is a *Pachysolen*. In another aspect, the yeast is *Pachysolen tannophilus*. In another aspect, the yeast is a *Pichia*. In another aspect, the yeast is a *Pichia stipitis*. In another aspect, the yeast is a *Bretannomyces*. In another aspect, the yeast is *Bretannomyces clausenii* (Philippidis, 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis*, *Clostridium acetobutylicum*, *Clostridium thermocellum*, *Clostridium phytofermentans*, *Geobacillus* sp., *Thermoanaerobacter saccharolyticum*, and *Bacillus coagulans* (Philippidis, 1996, supra).

In one aspect, the bacterium is a *Zymomonas*. In one aspect, the bacterium is *Zymomonas mobilis*. In another aspect, the bacterium is a *Clostridium*. In another aspect, the bacterium is *Clostridium acetobutylicum*. In another aspect, the bacterium is *Clostridium phytofermentan*. In another aspect, the bacterium is *Clostridium thermocellum*. In another aspect, the bacterium is *Geobacilus* sp. In another aspect, the bacterium is *Thermoanaerobacter saccharolyticum*. In another aspect, the bacterium is *Bacillus coagulans*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, Wisc., USA), BIOFERM™ AFT and XR (available from NABC—North American Bioproducts Corporation, Ga., USA), GERT STRAND™ (available from Gert Strand AB, Sweden), and FERMIOL™ (available from DSM Specialties).

In one aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 2003/062430, xylose isomerase).

In one aspect, the genetically modified fermenting organism is *Saccharomyces cerevisiae*. In another aspect, the genetically modified fermenting organism is *Zymomonas mobilis*. In another aspect, the genetically modified fermenting organism is *Escherichia coli*. In another aspect, the genetically modified fermenting organism is *Klebsiella oxytoca*. In another aspect, the genetically modified fermenting organism is *Kluyveromyces* sp.

It is well known in the art that the organisms described above can also be used to produce other substances, as described herein.

The fermenting organism is typically added to the degraded cellulosic material or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In one aspect, the yeast and/or another organism may be applied to the degraded cellulosic material and the fermentation is performed for about 12 hours to about 96 hours, such as 24-60 hours. In one aspect, the temperature is between about 20° C. to about 60° C., e.g., about 25° C. to about 50° C., or about 32° C. to about 50° C., and the pH is generally from about pH 3 to about pH 7, e.g., around pH 4-7, such as about pH 5. However, some fermenting organisms, e.g., bacteria, have higher fermentation temperature optima. Yeast or another microorganism is preferably applied in amounts of approximately $10^5$ to $10^{12}$, e.g., from approximately $10^7$ to $10^{10}$, especially approximately $2 \times 10^8$ viable cell count per mL of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry may be distilled to extract the ethanol. The ethanol obtained according to a process of the invention can be used as, e.g., fuel ethanol, drinking ethanol, i.e., potable neutral spirits, or industrial ethanol.

Fermentation Stimulators

A fermentation stimulator can be used in the processes described herein to further improve the fermentation, and in particular, the performance of the fermenting organism, such as, rate enhancement and product yield (e.g., ethanol yield). A "fermentation stimulator" refers to stimulators for growth of the fermenting organisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

According to the invention the (desired) fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, and octene); and a gas (e.g., methane, hydrogen ($H_2$), carbon dioxide ($CO_2$), and carbon monoxide (CO)). The fermentation product can also be protein as a high value product.

In one aspect, the fermentation product is an alcohol. It will be understood that the term "alcohol" encompasses a substance that contains one or more hydroxyl moieties. In one aspect, the alcohol is arabinitol. In another aspect, the alcohol is butanol. In another aspect, the alcohol is ethanol. In another aspect, the alcohol is glycerol. In another aspect, the alcohol is methanol. In another aspect, the alcohol is 1,3-propanediol. In another aspect, the alcohol is sorbitol. In another aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another aspect, the fermentation product is an organic acid. In one aspect, the organic acid is acetic acid. In another aspect, the organic acid is acetonic acid. In another aspect, the organic acid is adipic acid. In another aspect, the organic acid is ascorbic acid. In another aspect, the organic acid is citric acid. In another aspect, the organic acid is 2,5-diketo-D-gluconic acid. In another aspect, the organic acid is formic acid. In another aspect, the organic acid is fumaric acid. In another aspect, the organic acid is glucaric acid. In another aspect, the organic acid is gluconic acid. In another aspect, the organic acid is glucuronic acid. In another aspect, the organic acid is glutaric acid. In another aspect, the organic acid is 3-hydroxypropionic acid. In another aspect, the organic acid is itaconic acid. In another aspect, the organic acid is lactic acid. In another aspect, the organic acid is malic acid. In another aspect, the organic acid is malonic acid. In another aspect, the organic acid is oxalic acid. In another aspect, the organic acid is propionic acid. In another aspect, the organic acid is succinic acid. In another aspect, the organic acid is xylonic acid. See, for example, Chen and Lee, 1997, *Appl. Biochem. Biotechnol.* 63-65: 435-448.

In another aspect, the fermentation product is a ketone. It will be understood that the term "ketone" encompasses a substance that contains one or more ketone moieties. In another aspect, the ketone is acetone. See, for example, Qureshi and Blaschek, 2003, supra.

In another aspect, the fermentation product is an amino acid. In one aspect, the amino acid is aspartic acid. In another aspect, the amino acid is glutamic acid. In another aspect, the amino acid is glycine. In another aspect, the amino acid is lysine. In another aspect, the amino acid is serine. In another aspect, the amino acid is threonine. See, for example, Richard and Margaritis, 2004, *Biotechnology and Bioengineering* 87(4): 501-515.

In another aspect, the fermentation product is an alkane. The alkane can be an unbranched or a branched alkane. In one aspect, the alkane is pentane. In another aspect, the alkane is hexane. In another aspect, the alkane is heptane. In another aspect, the alkane is octane. In another aspect, the alkane is nonane. In another aspect, the alkane is decane. In another aspect, the alkane is undecane. In another aspect, the alkane is dodecane.

In another aspect, the fermentation product is a cycloalkane. In one aspect, the cycloalkane is cyclopentane. In another aspect, the cycoalkane is cyclohexane. In another aspect, the cycloalkane is cycloheptane. In another aspect, the cycloalkane is cyclooctane.

In another aspect, the fermentation product is an alkene. The alkene can be an unbranched or a branched alkene. In one aspect, the alkene is pentene. In another aspect, the alkene is hexene. In another aspect, the alkene is heptene. In another aspect, the alkene is octene.

In one aspect, the fermentation product is isoprene. In another aspect, the fermentation product is polyketide.

In another aspect, the fermentation product is a gas. In one aspect, the gas is methane. In another aspect, the gas is $H_2$. In another aspect, the gas is $CO_2$. In another aspect, the gas is CO. See, for example, Kataoka et al., 1997, *Water Science and Technology* 36(6-7): 41-47; and Gunaseelan, 1997, *Biomass and Bioenergy* 13(1-2): 83-114.

Recovery

The fermentation product can optionally be recovered after fermentation using any method known in the art including, but not limited to, chromatography, electrophoretic procedures, differential solubility, distillation, or extraction. For example, alcohol is separated from the fermented sugar cane trash and purified by conventional methods of distillation. For instance, ethanol with a purity of up to about 96 vol. % can be obtained, which can be used as, for example, fuel ethanol, drinking ethanol, i.e., potable neutral spirits, or industrial ethanol.

ENZYMES

Below sections describe polypeptides and enzymes that may be used according to the processes of the invention.

Phenol Oxidizing Enzymes

A phenol oxidizing enzyme used according to the invention may be any phenol oxidizing enzyme. The phenol oxidizing enzyme may be of any origin, but preferably of fungal or bacterial origin.

The phenol oxidizing enzyme(s) may belong to any of the following EC classes including: Laccase (EC 1.10.3.2), Catechol oxidase (EC 1.10.3.1), o-Aminophenol oxidase (1.10.3.4); and Monophenol monooxygenase (1.14.18.1). Laccases are preferred.

Laccases

Laccases (EC 1.10.3.2.) are multi-copper-containing enzymes that catalyze the oxidation of phenolic compounds. Laccases are produced by plants, bacteria and also a wide variety of fungi, including Ascomycetes such as *Aspergillus*, *Neurospora*, and *Podospora*; Deuteromycete including *Botrytis*, and Basidiomycetes such as *Collybia, Fomes,* *Lentinus, Pleurotus, Trametes*, and perfect forms of *Rhizoctonia*. A number of fungal laccases have been isolated. For example, Choi et al. (*Mol. Plant-Microbe Interactions* 5: 119-128, 1992) describe the molecular characterization and cloning of the gene encoding the laccase of the chestnut blight fungus, *Cryphonectria parasitica*. Kojima et al. (*J. Biol. Chem.* 265: 15224-15230, 1990; JP 2-238885) provide a description of two allelic forms of the laccase of the white-rot basidiomycete *Coriolus hirsutus*. Germann and Lerch (*Experientia* 41: 801 (1985); PNAS USA 83: 8854-8858 (1986)) have reported the cloning and partial sequencing of the Neurospora crassa laccase gene. Saloheimo et a/. (*J. Gen. Microbiol.* 137: 1537-1544 (1985); WO 92/01046) have disclosed a structural analysis of the laccase gene from the fungus *Phlebia radiata*.

Especially contemplated laccases include those derived from a strain of *Polyporus*, preferably *Polyporus pinsitus*; *Melanocarpus*, preferably *Melanocarpus albomyces; Myceliophthora*, preferably *Myceliophthora thermophila; Coprinus*, preferably *Coprinus cinereus*; *Rhizoctonia*, preferably *Rhizoctonia solani* or *Rhizoctonia praticola*; *Scytalidium*, preferably *Scytalidium thermophilum*; *Pyricularia*, preferably *Pyricularia oryzae*.

In an embodiment the laccase is derived from the tree *Rhus vernicifera* (Yoshida, 1883, Chemistry of Lacquer (Urushi) part 1. *J. Chem. Soc.* 43: 472-486).

In another embodiment the laccase is derived from *Polyporus pinsitus*, e.g., the one described in WO 96/00290 (Novozymes).

Jonsson et al., 1998, *Appl. Microbiol. Biotechnol.* 49: 691-697, also disclose a suitable laccase derived from *Polyporus versicolar*.

Other laccases include the one derived from *Pyricularia oryzae* concerned in, e.g., Muralikrishna et al., 1995, *Appl. Environ. Microbiol.* 61(12): 4374-4377 or the laccase derived from *Scytalidium thermophilum* disclosed in *Abstract of Papers American Chemical Society* vol. 209, no. 1-2 (1995).

The laccase may also be one derived from *Coprinus cinereus*, e.g., the one concerned in Schneider et al., 1999, *Enzyme and Microbial Technology* 25: 502-508.

Other suitable laccases include those derived from *Rhizoctonia solani* concerned in Waleithner et al., 1996, *Curr. Genet.* 29: 395-403, or derived from *Melanocarpus albomyces* concerned in Kiiskinen et al., 2004, *Microbiology* 150: 3065-3074.

Suitable bacterial laccase include those derived from *Streptomyces coelicolor*, e.g., disclosed by Machczynski et al., 2004, *Protein Science* 13: 2388-2397.

In a preferred embodiment the laccase is derived from *Myceliophthora thermophila*, e.g., the one described in WO 95/33836 (Novozymes).

Contemplated laccases also include those comprising an amino acid sequence having at least 60%, at least 70% at least 80%, at least 85%, at least 90%, at least 95% identity, at least 97%, at least 98%, at least 99% identity to the *Myceliophthora thermophila* laccase disclosed in WO 95/33836 or any of the above mentioned laccases.

Hemicellulases

The hemicellulase used in a process of the invention may be any hemicellulase. The hemicellulase may be of any origin, but preferably of fungal or bacterial origin.

The term "hemicellulase" or "hemicellulolytic enzyme" means one or more (several) enzymes that hydrolyze a hemicellulosic material. See, for example, Shallom and Shoham, 2003, Microbial hemicellulases. *Current Opinion In Microbiology* 6(3): 219-228. Hemicellulases are key components in the degradation of plant biomass. Examples of hemicellulases include, but are not limited to, an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). A most informative and updated classification of these and other carbohydrate active enzymes is available on the Carbohydrate-Active Enzymes (CAZy) database. Hemicellulolytic enzyme activities can be measured according to Ghose and Bisaria, 1987, *Pure & Appl. Chem.* 59: 1739-1752.

Xylanases

In a preferred embodiment the hemicellulase is a "xylanase". The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

Examples of specifically contemplated xylanases include GH10 xylanases, such as one derived from a strain of the genus *Aspergillus*, such as a strain from *Aspergillus fumigatus*, such as the one disclosed as Xyl III in WO 2006/078256, or *Aspergillus aculeatus*, such as the one disclosed in WO 94/21785 as SEQ ID NO: 5 (Xyl II).

The xylanase for preconditioning according to the invention may be comprised in a cellulolytic enzyme preparation which further includes a xylanase. In one embodiment hemicellulase is a cellulolytic enzyme preparation further comprising a xylanase, preferably a GH10 xylanase, such as one derived from a strain of the genus *Aspergillus*, such as a strain from *Aspergillus fumigatus*, such as the one disclosed as Xyl III in WO 2006/078256, or *Aspergillus aculeatus*, such as the one disclosed in WO 94/21785 as SEQ ID NO: 5 (Xyl II).

Contemplated xylanases also include those comprising an amino acid sequence having at least 60%, at least 70%, at least 80%, at least 85%, at least 90%, at least 95% identity, at least 97%, at least 98%, at least 99% identity to the *Aspergillus fumigatus* Xyl III in WO 2006/078256 or the *Aspergillus aculeatus* xylanase disclosed in WO 94/21785 as SEQ ID NO: 5 (Xyl II).

Beta-xylosidases

In a preferred embodiment the hemicellulase used in a method or process of the invention is a "beta-xylosidase". The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN®20.

Examples of specifically contemplated beta-xylosidase includes the one derived from a strain of the genus *Aspergillus*, such as a strain of *Aspergillus fumigatus*, such as the one disclosed in U.S. provisional application No. 61/577,609 (Examples 16 and 17-SEQ ID NO: 15 [DNA sequence] and SEQ ID NO: 16 [deduced amino acid sequence]), or derived from a strain of *Trichoderma*, such as a strain of *Trichoderma reesei*, such as the mature polypeptide of SEQ ID NO: 58 in WO 2011/057140.

The beta-xylosidase used during preconditioning may be comprised in a cellulolytic enzyme preparation. In one embodiment the hemicellulase is a cellulolytic enzyme preparation further comprising a beta-xylosidase, such as one derived from a strain of the genus *Aspergillus*, such as a strain of *Aspergillus fumigatus* (e.g., one disclosed in WO 2011/057140), such as those disclosed in U.S. provisional application Nos. 61/526,833 and 61/577,609 (Examples 16 and 17-SEQ ID NO: 15 [DNA sequence] and SEQ ID NO: 16 [deduced amino acid sequence]), or derived from a strain of *Trichoderma*, such as a strain of *Trichoderma reesei*, such as the mature polypeptide of SEQ ID NO: 58 in WO 2011/057140.

Contemplated beta-xylosidases also include those comprising an amino acid sequence having at least 60%, at least 70% at least 80%, at least 85%, at least 90%, at least 95% identity, at least 97%, at least 98%, at least 99% identity to the *Aspergillus fumigatus* beta-xylosidase disclosed as SEQ ID NO: 206 in WO 2011/057140 or any of the beta-xylosidases mentioned herein.

The hemicellulase used for preconditioning is or may comprise a commercial hemicellulase product. Examples of commercial hemicellulase products include, for example, SHEARZYME™ (Novozymes NS), CELLIC™ HTec (Novozymes A/S), CELLIC™ HTec2 (Novozymes A/S), CELLIC™ HTec3 (Novozymes), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Cellulolytic Enzyme Preparations

A cellulolytic enzyme preparation is a preparation containing one or more (e.g., several) enzymes that hydrolyze cellulosic material. Such enzymes include endoglucanase, cellobiohydrolase, beta-glucosidase, or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, *Pure Appl. Chem.* 59: 257-68).

For purposes of the present invention, cellulolytic enzyme activity for, e.g., a cellulolytic enzyme preparation, may be determined by measuring the increase in hydrolysis of a cellulosic material by cellulolytic enzyme(s) under the following conditions: 1-50 mg of cellulolytic enzyme protein/g of cellulose in PCS (or other pretreated cellulosic material)

for 3-7 days at a suitable temperature, e.g., 50° C., 55° C., 60° C., or 65° C., compared to a control hydrolysis without addition of cellulolytic enzyme protein. Typical conditions are 1 ml reactions, washed or unwashed PCS, 5% insoluble solids, 50 mM sodium acetate pH 5, 1 mM MnSO$_4$, 50° C., 55° C., 60° C., or 65° C., 72 hours, sugar analysis by AMINEX® HPX-87H column (Bio-Rad Laboratories, Inc., Hercules, Calif., USA).

As mentioned above a cellulolytic enzyme preparation used for saccharification (hydrolysis) in a process of the invention typically comprises one or more endoglucanases, cellubiohydrolases and/or beta-glucosidases.

In an embodiment the cellulolytic enzyme preparation is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the cellulolytic enzyme preparation is derived from a strain of *Trichoderma reesei*.

The cellulolytic enzyme preparation may further comprise one or more of the following polypeptides, such as enzymes: GH61 polypeptide having cellulolytic enhancing activity, beta-glucosidase, xylanase, beta-xylosidase, CBHI, CBHII, or a mixture of two, three, four, five or six thereof.

The further polypeptide(s) (e.g., GH61 polypeptide) and/or enzyme(s) (e.g., beta-glucosidase, xylanase, beta-xylosidase, CBH1 and/or CBH ii) may be foreign to the cellulolytic enzyme preparation producing organism (e.g., *Trichoderma reesei*).

In an embodiment the cellulolytic enzyme preparation comprises a GH61 polypeptide having cellulolytic enhancing activity and a beta-glucosidase.

In another embodiment the cellulolytic enzyme preparation comprises a GH61 polypeptide having cellulolytic enhancing activity, a beta-glucosidase, and a CBHI. In another embodiment the cellulolytic enzyme preparation comprises a GH61 polypeptide having cellulolytic enhancing activity, a beta-glucosidase, a CBHI and a CBHII.

Other enzymes, such as endoglucanases, may also be comprises in the cellulolytic enzyme preparation.

Beta-Glucosidases

The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN®20.

The cellulolytic enzyme preparation may in one embodiment comprise one or more (e.g., several) beta-glucosidases. The beta-glucosidase may in one embodiment be one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or an *Aspergillus fumigatus* beta-glucosidase variant, such as one disclosed in WO 2012/044915 (hereby incorporated by reference), e.g., with one or more, preferably all, of the following substitutions: F100D, S283G, N456E, F512Y.

In another embodiment the beta-glucosidase is derived from a strain of the genus *Penicillium*, such as a strain of the *Penicillium brasilianum* disclosed in WO 2007/019442, or a strain of the genus *Trichoderma*, such as a strain of *Trichoderma reesei*.

Contemplated beta-glucosidases include those comprising an amino acid sequence having at least 60%, at least 70% at least 80%, at least 85%, at least 90%, at least 95% identity, at least 97%, at least 98%, at least 99% identity to the *Aspergillus oryzae* disclosed in WO 2002/095014, or the fusion protein having beta-glucosidase activity disclosed in WO 2008/057637.

Contemplated beta-glucosidases also include those comprising an amino acid sequence having at least 60%, at least 70% at least 80%, at least 85%, at least 90%, at least 95% identity, at least 97%, at least 98%, at least 99% identity to the *Aspergillus fumigatus* beta-glucosidase disclosed as amino acids 20 to 863 of SEQ ID NO: 2 in WO 2005/047499 (hereby incorporated by reference) or any of the beta-glucosidases mentioned above.

Polypeptides Having Cellulolytic Enhancing Activity

The term "polypeptide having cellulolytic enhancing activity" means a GH61 polypeptide that catalyzes the enhancement of the hydrolysis of a cellulosic material by enzyme having cellulolytic activity.

For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes NS, Bagsverd, Denmark) in the presence of 2-3% of total protein weight *Aspergillus oryzae* beta-glucosidase (recombinantly produced in *Aspergillus oryzae* according to WO 02/95014) or 2-3% of total protein weight *Aspergillus fumigatus* beta-glucosidase (recombinantly produced in *Aspergillus oryzae* as described in WO 02/95014) of cellulase protein loading is used as the source of the cellulolytic activity.

The term "Family 61 glycoside hydrolase" or "Family GH61" or "GH61" means a polypeptide falling into the glycoside hydrolase Family 61 according to Henrissat, 1991, *Biochem. J.* 280: 309-316, and Henrissat and Bairoch, 1996, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are certainly non-canonical and they cannot be considered as bona fide glycosidases. However, they are kept in the CAZy classification on the basis of their capacity to enhance the breakdown of cellulose when used in conjunction with a cellulolytic enzyme.

GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

The cellulolytic enzyme preparation may in one embodiment comprise one or more GH61 polypeptide having cellulolytic enhancing activity. In one embodiment the cellulolytic enzyme preparation comprises a GH61 polypeptide having cellulolytic enhancing activity, such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 8; or one derived from a strain of *Aspergillus*, such as a strain of *Aspergillus fumigatus*, such as the one described in WO 2010/138754 as SEQ ID NO: 2; or one derived from a strain derived from *Penicillium*, such as a strain of *Penicillium emersonii*, such as the one disclosed in WO 2011/041397.

Contemplated GH61 polypeptides also include those comprising an amino acid sequence having at least 60%, at least 70% at least 80%, at least 85%, at least 90%, at least 95% identity, at least 97%, at least 98%, at least 99% identity to the *Thermoascus aurantiacus*, GH61 polypeptide disclosed in WO 2005/074656 as SEQ ID NO: 2, the *Thielavia terrestris* GH61 polypeptide disclosed in WO 2005/074647 as SEQ ID NO: 8, or the *Penicillium emersonii* GH61 polypeptide disclosed in WO 2011/041397(all refs hereby incorporated by reference).

Cellobiohydrolases

The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teed, 1997, *Trends in Biotechnology* 15: 160-167; Teeri et al., 1998, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581. In the present invention, the Tomme et al. method can be used to determine cellobiohydrolase activity.

CBH I

The cellulolytic enzyme preparation may in one embodiment comprise one or more CBH I (cellobiohydrolase I). In one embodiment the cellulolytic enzyme preparation comprises a cellobiohydrolase I (CBH I), such as one derived from a strain of the genus *Aspergillus*, such as a strain of *Aspergillus fumigatus*, such as the Cel7A CBHI disclosed as SEQ ID NO: 2 in WO 2011/057140, or a strain of the genus *Trichoderma*, such as a strain of *Trichoderma reesei*.

Contemplated CBH I enzymes also include those comprising an amino acid sequence having at least 60%, at least 70% at least 80%, at least 85%, at least 90%, at least 95% identity, at least 97%, at least 98%, at least 99% identity to the Cel7A CBH I from *Aspergillus fumigatus* disclosed as SEQ ID NO: 2 in WO 2011/057140 (hereby incorporated by reference).

CBH II

The cellulolytic enzyme preparation may in one embodiment comprise one or more CBH II (cellobiohydrolase II). In one embodiment the cellobiohydrolase II (CBHII), such as one derived from a strain of the genus *Aspergillus*, such as a strain of *Aspergillus fumigatus*; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

Contemplated CBH II enzymes also include those comprising an amino acid sequence having at least 60%, at least 70% at least 80%, at least 85%, at least 90%, at least 95% identity, at least 97%, at least 98%, at least 99% identity to the CBH II derived from *Aspergillus fumigatus* disclosed as SEQ ID NO: 3 [DNA sequence] and SEQ ID NO: 4 (deduced amino acid sequence in co-pending U.S. provisional application No. 61/577,609 (hereby incorporated by reference).

Endoglucanases

The term "endoglucanase" means an endo-1,4-(1,3;1,4)-beta-D-glucan 4-glucanohydrolase (E.C. 3.2.1.4), which catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

As mentioned above the cellulolytic enzyme preparation may comprise a number of difference polypeptides, including enzymes.

In an embodiment the cellulolytic enzyme preparation comprises a *Trichoderma reesei* cellulolytic preparation, further comprising *Thermoascus aurantiacus* GH61A polypeptide having cellulolytic enhancing activity (WO 2005/074656), and *Aspergillus oryzae* beta-glucosidase fusion protein (WO 2008/057637).

In another embodiment the cellulolytic enzyme preparation comprises a *Trichoderma reesei* cellulolytic enzyme preparation, further comprising *Thermoascus aurantiacus* GH61A polypeptide having cellulolytic enhancing activity (SEQ ID NO: 2 in WO 2005/074656), and *Aspergillus fumigatus* beta-glucosidase (SEQ ID NO: 2 of WO 2005/047499).

In another embodiment the cellulolytic enzyme preparation comprises a *Trichoderma reesei* cellulolytic enzyme preparation further comprising *Penicillium emersonii* GH61A polypeptide having cellulolytic enhancing activity disclosed in WO 2011/041397, and *Aspergillus fumigatus* beta-glucosidase (SEQ ID NO: 2 of WO 2005/047499).

In another embodiment the cellulolytic enzyme preparation comprises a *Trichoderma reesei* cellulolytic enzyme preparation further comprising *Penicillium emersonii* GH61A polypeptide having cellulolytic enhancing activity disclosed in WO 2011/041397, and *Aspergillus fumigatus* beta-glucosidase variant disclosed in WO 2012/044915 (hereby incorporated by reference), the following substitutions: F100D, S283G, N456E, F512Y.

In an embodiment the cellulolytic enzyme preparation also comprises a xylanase (e.g., derived from *Aspergillus aculeatus* or *Aspergillus fumigatus*) and/or a beta-xylosidase (e.g., derived from *Aspergillus fumigatus*).

In an embodiment the cellulolytic enzyme preparation comprises a *Trichoderma reesei* cellulolytic preparation, further comprising *Thermoascus aurantiacus* GH61A polypeptide having cellulolytic enhancing activity (WO 2005/

074656), *Aspergillus oryzae* beta-glucosidase fusion protein (WO 2008/057637), and *Aspergillus aculeatus* xylanase (Xyl II in WO 94/21785).

In another embodiment the cellulolytic enzyme preparation comprises a *Trichoderma reesei* cellulolytic preparation, further comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785).

In another embodiment the cellulolytic enzyme preparation comprises a *Trichoderma reesei* cellulolytic preparation, further comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 of WO 2005/047499) and *Aspergillus aculeatus* xylanase (Xyl II disclosed in WO 94/21785).

In another embodiment the cellulolytic enzyme preparation comprises a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499) and *Aspergillus fumigatus* xylanase (Xyl III in WO 2006/078256).

In another embodiment the cellulolytic enzyme preparation comprises a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499), *Aspergillus fumigatus* xylanase (Xyl III in WO 2006/078256), and Cel7A CBH I from *Aspergillus fumigatus* disclosed as SEQ ID NO: 2 in WO 2011/057140.

In another embodiment the cellulolytic enzyme preparation comprises a *Trichoderma reesei* cellulolytic preparation further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499), *Aspergillus fumigatus* xylanase (Xyl III in WO 2006/078256), Cel7A CBH I from *Aspergillus fumigatus* disclosed as SEQ ID NO: 2 in WO 2011/057140, and CBH II derived from *Aspergillus fumigatus* disclosed in co-pending US provisional No. 61/577,609 as SEQ ID NO: 3 [DNA sequence] and SEQ ID NO: 4 (deduced amino acid sequence).

In another embodiment the cellulolytic enzyme preparation comprises a *Trichoderma reesei* cellulolytic preparation further comprising *Penicillium emersonii* GH61A polypeptide having cellulolytic enhancing activity disclosed in WO 2011/041397, Aspergillus fumigatus beta-glucosidase variant disclosed in co-pending US provisional application No. 61/388,997 (hereby incorporated by reference) with the following substitutions: F100D, S283G, N456E, F512Y, *Aspergillus fumigatus* xylanase (Xyl III in WO 2006/078256), Cel7A CBH I from *Aspergillus fumigatus* disclosed as SEQ ID NO: 2 in WO 2011/057140, and CBH II derived from *Aspergillus fumigatus* disclosed in U.S. provisional application no. 61/577,609 as SEQ ID NO: 3 [DNA sequence] and SEQ ID NO: 4 (deduced amino acid sequence).

All cellulolytic enzyme preparations disclosed in U.S. provisional application No. 61/577,609 are also contemplated and hereby incorporated by reference.

The cellulolytic enzyme preparation comprises or may further comprise one or more (several) proteins selected from the group consisting of a cellulase, a GH61 polypeptide having cellulolytic enhancing activity, a hemicellulase, an expansin, an esterase, a laccase, a ligninolytic enzyme, a pectinase, a peroxidase, a protease, and a swollenin.

In an embodiment the cellulolytic enzyme preparation is or comprises a commercial cellulolytic enzyme preparation.

Examples of commercial cellulolytic enzyme preparations suitable for use in the present invention include, for example, CELLIC™ CTec (Novozymes NS), CELLIC™ Ctec2 (Novozymes NS), CELLIC™ Ctec3 (Novozymes NS), CELLUCLAST™ (Novozymes NS), NOVOZYM™ 188 (Novozymes NS), CELLUZYME™ (Novozymes NS), CEREFLO™ (Novozymes NS), and ULTRAFLO™ (Novozymes NS), ACCELERASE™ (Genencor Int.), LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.).

The cellulolytic enzyme preparation may be added during saccharification in amounts effective from about 0.001 to about 5.0 wt. % of solids(TS), more preferably from about 0.025 to about 4.0 wt. % of solids, and most preferably from about 0.005 to about 2.0 wt. % of solids (TS).

The present invention is further described by the following examples that should not be construed as limiting the scope of the invention.

Material & Methods

Materials:

Laccase A: Laccase derived from *Myceliophthora thermophila* disclosed in WO 95/33836.

Hemicellulase A: Cellulolytic enzyme preparation from *Trichoderma reesei* comprising xylanase derived from *Aspergillus aculeatus* (Xyl II disclosed in WO 94/21785).

Cellulolytic Enzyme Preparation A: Cellulolytic enzyme preparation from *Trichoderma reesei*, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499).

TAPPI Standard method: Water retention value (WRV); TAPPI: UM 256; Issued prior to 1991; Reviewed and retained in the UM SET-2011; ©2011 TAPPI.

EXAMPLE 1

Unwashed dilute acid pretreated corn stover (uwPCS). The pH value of the uwPCS was adjusted to 5.1 with 50% NaOH solution. The total solids (TS) contain was measured with moisture analyzer. The predetermined amount of the pH adjusted uwPCS was added into a kettle reactor. The initial water, penicillin solution and preconditioning enzyme, laccase (i.e., Laccase A, 25 micrograms Enzyme Protein/g cellulose)) and/or hemicellulase (i.e., Hemicellulase A, 250 micrograms Enzyme Protein/g cellulose), solutions was added. The TS for preconditioning was 22%. The preconditioning was carried out overnight at 50° C. After preconditioning, the pH was checked and adjusted to 5.0 if needed. After pH adjustment, the hydrolysis enzyme (Cellulolytic Enzyme Preparation A) and make up water were added. The final TS for hydrolysis were 20%. The enzymatic hydrolysis was performed at 50° C. for 5 days. After enzymatic hydrolysis, 100 g of hydrolysate was taken out and the liquid was separated from solid with a TAPPI standard method (UM 256 for water retention value), centrifuging whole slurry at 900 g for 30 min. The results of separated liquids are shown in Table 1. The liquid yield was improved from 72.8% to 77.6% with hemicellulase only and to 81.6% with laccase/hemicellulase combination, respectively.

TABLE 1

Liquid yield from enzymatic hydrolysate

| Preconditioning | Volume of separated liquid (ml/100 ml hydrolysate) | Total sugar from separated liquor (g) | |
|---|---|---|---|
| | | Glucose (g) | Xylose (g) |
| Control, preconditioned without enzymes | 72.8 | 5.37 | 3.61 |
| Preconditioned with Laccase A only | 73.5 | 5.58 | 3.72 |
| Preconditioned with Hemicellulase A only | 77.6 | 5.78 | 3.83 |
| Preconditioned with Laccase A and Hemicellulase A | 81.6 | 6.15 | 4.05 |

EXAMPLE 2

Unwashed dilute acid pretreated corn stover (uwPCS). The pH value of the uwPCS was adjusted to 5.1 with 50% NaOH solution. The total solids (TS) contain was measured with moisture analyzer. The predetermined amount of the pH adjusted uwPCS was added into a kettle reactor. The predetermined amount of penicillin solution was added and mixed well. Well mixed uwPCS was preconditioned overnight at 50° C. with and without laccase (Laccase A, 25 micrograms EP/g cellulose). The final TS for preconditioning was 30%. After preconditioning, the treated uwPCS was squeezed and the liquor was collected and the results are shown in Table 2. Compared with control, more than 11% extra liquor was obtained by laccase treatment.

TABLE 2

Liquid yield from the preconditioned uwPCS

| Preconditioning | Volume of separated liquid (ml/290 g uwPCS) | Total sugar from separated liquor (g) |
|---|---|---|
| Control, preconditioned without enzymes | 99.5 | 9.72 (glucose + xylose) |
| Preconditioned with laccase only | 110.7 | 11.31 (glucose + xylose) |

The invention is further described in the following paragraphs:

1. A process of producing a fermentation product from pretreated cellulosic material, comprising the steps of:
   i) preconditioning a pretreated cellulosic material;
   ii) hydrolysis using a cellulolytic enzyme preparation;
   iii) fermenting sugars with a microorganism;
   wherein a solid-liquid separation step, resulting in a solid fraction and a liquid fraction, is carried out:
   a) after preconditioning, but before hydrolysis; or
   b) after hydrolysis, but before fermentation;
   wherein a phenol oxidizing enzyme and/or a hemicellulase are present or added:
   during preconditioning; or
   after preconditioning, but before hydrolysis; or
   during hydrolysis.
2. The process of paragraph 1, wherein a phenol oxidizing enzyme is present or added:
   during preconditioning; or
   after preconditioning, but before hydrolysis; or
   during hydrolysis.
3. The process of paragraph 1, wherein a hemicellulase is present or added:
   during preconditioning; or
   after preconditioning, but before hydrolysis; or
   during hydrolysis.
4. The process of paragraph 1, wherein a phenol oxidizing enzyme and a hemicellulase are present or added:
   during preconditioning; or
   after preconditioning, but before hydrolysis; or
   during hydrolysis.
5. The process of any of paragraphs 1-4, wherein the phenol oxidizing enzyme is a laccase.
6. The process of any of paragraphs 1-5, wherein the hemicellulase is selected from a xylanase (e.g., an *Aspergillus aculeatus* or *Aspergillus fumigatus* xylanase), and a xylosidase (e.g., *Aspergillus fumigatus* beta-xylosidase).
7. The process of any of paragraphs 1-6, wherein the cellulosic material is un-detoxified.
8. The process of any of paragraphs 1-6, wherein the cellulosic material is unwashed.
9. The process of any of paragraphs 1-8, wherein the solid-liquid separation is carried out after preconditioning, but before hydrolysis.
10. The process of any of paragraphs 1-9, wherein the pretreated cellulosic material is dilute acid pretreated cellulosic material.
11. The process of any of paragraphs 1-10, wherein the solid fraction resulting from the solid-liquid separation step, is hydrolyzed and then fermented.
12. The process of any of paragraphs 1-11, wherein the liquid fraction resulting from the solid-liquid separation step, is fermented.
13. The process of any of paragraphs 1-12, wherein the fermentation product from the solid fraction and/or the liquid fraction fermentation(s) is/are, optionally recovered.
14. The process of any of paragraphs 1-13, wherein the liquid fraction is detoxified after solid-liquid separation.
15. The process of paragraph 14, wherein the detoxified liquid fraction is hydrolyzed together with the solid fraction and then fermented.
16. The process of any of paragraphs 1-15, wherein the solid fraction resulting from the solid-liquid separation step, is hydrolyzed and then fermented together with the liquid fraction resulting from the solid-liquid separation step.
17. The process of any of paragraphs 1-16, wherein the solid-liquid separation is carried out after hydrolysis, but before fermentation.
18. The process of any of paragraphs 1-17, wherein the liquid fraction resulting from the solid-liquid separation step, is fermented and optionally recovered.
19. The process of any of paragraphs 1-18, wherein the pretreated cellulosic material is auto-hydrolyzed pretreated cellulosic material.
20. The process of paragraph 19, wherein solid-liquid separation is carried out after preconditioning, but before hydrolysis.

21. The process of paragraph 19 or 20, wherein the solid fraction resulting from solid-liquid separation, is hydrolyzed and then fermented.
22. The process of any of paragraphs 1-21, wherein the liquid fraction resulting from the solid-liquid separation, is reused as water in fermentation.
23. The process of any of paragraphs 1-22, wherein the solid-liquid separation is carried out after hydrolysis, but before fermentation.
24. The process of any of paragraphs 1-203, wherein the solid fraction resulting from the solid liquid separation, is fermented and optional recovered.
25. The process of any of paragraphs 1-24, wherein hydrolysis is carried out at 10-40% TS, such as 15-35% TS, such as 20-30% TS.
26. The process of any of paragraphs 1-25, wherein the cellulosic material is pretreated unwashed corn stover (PCS), corn cob, wheat straw, rice straw and switch grass.
27. The process of any of paragraphs 1-26, wherein preconditioning occurs at 5-50% TS, such as 10-40% TS, such as 15-35% TS, such as 20-30% TS.
28. The process of any of paragraphs 1-27, wherein the preconditioning occurs for at least 30 minutes, e.g., at least 1 hour, 2, hours, 4 hours, 8 hours, 12 hours, or 24 hours, such as 30 minutes to 24 hours.
29. The process of any of paragraphs 1-28, wherein the preconditioning occurs at a temperature between 20-70° C., such as between 40 and 60° C., such as around 50° C.
30. The process of any of paragraphs 1-29, wherein the phenol oxidizing enzyme, especially laccase, loading is between 1-500 micrograms EP/g cellulose, such as 5-100 micrograms EP/g cellulose.
31. The process of any of paragraphs 1-30, wherein the hemicellulase loading is between 0.01 and 20 mg EP/cellulose, such as 0.1-1 mg EP/g cellulose.
32. A process of any of paragraphs 1-31, comprising the steps of:
preconditioning a pretreated cellulosic material;
solid-liquid separation resulting in a solid fraction and a liquid fraction;
hydrolyzing the solid fraction using a cellulolytic enzyme preparation;
fermenting sugars from the hydrolyzed solid fraction, and/or optionally the liquid fraction, with a microorganism;
wherein a phenol oxidizing enzyme and/or a hemicellulase are present or added:
during preconditioning; or
after preconditioning, but before hydrolysis;
during hydrolysis.
33. The process of paragraph 32, wherein a phenol oxidizing enzyme is present or added:
during preconditioning; or
after preconditioning, but before hydrolysis; or
during hydrolysis.
34. The process of paragraph 32, wherein a hemicellulase is present or added:
during preconditioning; or
after preconditioning, but before hydrolysis; or
during hydrolysis.
35. The process of paragraph 32, wherein a phenol oxidizing enzyme and a hemicellulase are present or added:
during preconditioning; or
after preconditioning, but before hydrolysis; or
during hydrolysis.
36. The process of any of paragraphs 32-35, wherein the pretreated cellulosic material is dilute acid pretreated cellulosic material.
37. The process of any of paragraphs 32-36, further comprising recovering the fermented material, e.g., by distillation.
38. A process of any of paragraphs 32-37, wherein the pretreated cellulosic material is auto hydrolyzed acid pretreated cellulosic material.
39. The process of any of paragraphs 32-38, wherein the solid fraction resulting from the solid-liquid separation is hydrolyzed and then fermented.
40. The process of any of paragraphs 32-39, wherein the liquid fraction resulting from the solid-liquid separation is reused as water in fermentation.
41. The process of any of paragraphs 32-40, further comprising recovering the fermentation product, e.g., by distillation.
42. The process of any of paragraphs 1-41, comprising the steps of:
preconditioning a pretreated cellulosic material;
hydrolyzing the pretreated cellulosic material using a cellulolytic enzyme preparation;
solid-liquid separation;
fermenting the sugars from the liquid fraction with a microorganism;
wherein a phenol oxidizing enzyme and/or a hemicellulase are present or added:
during preconditioning; or
after preconditioning, but before hydrolysis;
during hydrolysis.
43. The process of paragraph 42, wherein a phenol oxidizing enzyme is present or added:
during preconditioning; or
after preconditioning, but before hydrolysis; or
during hydrolysis.
44. The process of paragraph 42, wherein a hemicellulase is present or added:
during preconditioning; or
after preconditioning, but before hydrolysis; or
during hydrolysis.
45. The process of paragraph 42, wherein a phenol oxidizing enzyme and a hemicellulase are present or added:
during preconditioning; or
after preconditioning, but before hydrolysis; or
during hydrolysis.
46. The process of any of paragraphs 42-45, wherein the pretreated cellulosic material is dilute acid pretreated cellulosic material.
47. The process of any of paragraphs 42-46, further comprising recovering the fermentation product, e.g., by distillation.
48. The process of any of paragraphs 1-47, comprising the steps of:
preconditioning a pretreated cellulosic material;
hydrolysis of the pretreated cellulosic material using a cellulolytic enzyme preparation;
solid-liquid separation;
fermenting the sugars from the solid fraction with a microorganism;
wherein a phenol oxidizing enzyme and/or a hemicellulase are present or added:
during preconditioning; or
after preconditioning, but before hydrolysis;
during hydrolysis.
49. The process of paragraph 48, wherein a phenol oxidizing enzyme is present or added:

during preconditioning; or
after preconditioning, but before hydrolysis; or
during hydrolysis.
50. The process of paragraph 48, wherein a hemicellulase is present or added:
during preconditioning; or
after preconditioning, but before hydrolysis; or
during hydrolysis.
51. The process of paragraph 48, wherein a phenol oxidizing enzyme and a hemicellulase are present or added:
during preconditioning; or
after preconditioning, but before hydrolysis; or
during hydrolysis.
52. The process of any of paragraphs 48-51, wherein the pretreated cellulosic material is auto-hydrolyzed pretreated cellulosic material.
53. The process of any of paragraphs 48-52, further comprising recovering the fermentation product, e.g., by distillation.
54. The process of any of paragraphs 1-53, wherein hydrolysis and fermentation are carried out as separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC).
55. The process of any of paragraphs 1-54, wherein the cellulolytic enzyme preparation is of fungal origin.
56. The process of any of paragraphs 1-55, wherein the cellulolytic enzyme preparation is derived from Trichoderma (e.g., Trichoderma reesei).
57. The process of any of paragraphs 1-56, wherein saccharification is carried out in the presence a cellulolytic enzyme preparation including enzyme activities selected from the group of endoglucanase, cellobiohydrolase, and beta-glucosidase (e.g., *Aspergillus fumigatus* or *Aspergillus oryzae* beta-glucosidase).
58. The process of any of paragraphs 1-57, further wherein saccharification is carried out using a polypeptide having cellulolytic enhancing activity (e.g., a *Thermoascus aurantiacus* or *Penicilluim emersonii* cellulolytic enhancing polypeptide).
59. The process of any of paragraphs 1-58, further wherein saccharification is carried out using one or more enzymes selected from hemicellulase, expansin, esterase, laccase, ligninolytic enzyme, pectinase, peroxidase, protease, and swollenin.
60. The process of any of paragraphs 1-59, wherein the hemicellulase is selected from a xylanase (e.g., an *Aspergillus aculeatus* or *Aspergillus fumigatus* xylanase), and a xylosidase (e.g., *Aspergillus fumigatus* beta-xylosidase).
61. The process of any of paragraphs 1-60, wherein the fermentation product is an alcohol (e.g., ethanol or butanol), an organic acid, a ketone, an amino acid, or a gas.
62. The process of any of paragraphs 1-61, wherein the process results in an increased solid-liquid separation compared to when no phenol oxidizing enzyme and hemicellulase are present or added.
63. A process of producing sugars from pretreated cellulosic material comprising the steps of:
(a) preconditioning a pretreated cellulosic material;
(b) hydrolysis of the pretreated cellulosic material using a cellulolytic enzyme preparation;
wherein a solid-liquid separation step, resulting in a solid fraction and a liquid fraction, is carried out:
(i) after preconditioning, but before hydrolysis; or
(ii) after hydrolysis;
wherein a phenol oxidizing enzyme and/or a hemicellulase are present or added:
during preconditioning; or
after preconditioning, but before hydrolysis;
during hydrolysis.
64. The process of paragraph 63, wherein a phenol oxidizing enzyme is present or added:
during preconditioning; or
after preconditioning, but before hydrolysis; or
during hydrolysis.
65. The process of paragraph 63, wherein a hemicellulase is present or added:
during preconditioning; or
after preconditioning, but before hydrolysis; or
during hydrolysis.
66. The process of paragraph 63, wherein a phenol oxidizing enzyme and a hemicellulase are present or added:
during preconditioning; or
after preconditioning, but before hydrolysis; or
during hydrolysis.
67. A process for producing a fermentation product, comprising:
(a) preconditioning a pretreated cellulosic material with a phenol oxidizing enzyme and/or a hemicellulase;
(b) hydrolyzing the pretreated cellulosic material using a cellulolytic enzyme preparation;
(c) solid-liquid separation of the pretreated cellulosic material resulting in a solid fraction and a liquid fraction;
(d) fermenting sugars with a microorganism;
wherein the preconditioning occurs prior to or during hydrolysis and the solid-liquid separation occurs after preconditioning but before hydrolysis, or after hydrolysis but before fermentation.
68. The process of paragraph 67, wherein the preconditioning is with a phenol oxidizing enzyme.
69. The process of paragraph 67, wherein the preconditioning is with a hemicellulase.
70. The process of paragraph 67, wherein the preconditioning is with a phenol oxidizing enzyme and a hemicellulase.
71. The process of any of paragraphs 67-70, wherein the preconditioning occurs prior to hydrolysis.
72. The process of any of paragraphs 67-71, wherein the preconditioning occurs during hydrolysis.
73. The process of any of paragraphs 67-72, wherein the solid-liquid separation occurs after preconditioning but before hydrolysis.
74. The process of any of paragraphs 67-73, wherein the solid-liquid separation occurs after hydrolysis but before fermentation.
75. The process of any of paragraphs 67-74, wherein the solid fraction resulting from the solid-liquid separation step, is hydrolyzed and then fermented.
76. The process of any of paragraphs 67-75, wherein the liquid fraction resulting from the solid-liquid separation step, is fermented.
77. The process of any of paragraphs 67-76, further comprising detoxifying the liquid fraction after solid-liquid separation.
78. The process of paragraph 77, wherein the detoxified liquid fraction is hydrolyzed together with the solid fraction and then fermented.
79. The process of any of paragraphs 67-78, wherein the solid fraction resulting from the solid-liquid separation step, is hydrolyzed and then fermented together with the liquid fraction resulting from the solid-liquid separation step.

80. The process of any of paragraphs 67-79, wherein the solid-liquid separation is carried out after hydrolysis, but before fermentation.

81. The process of any of paragraphs 67-80, wherein the liquid fraction resulting from the solid-liquid separation step, is fermented.

82. The process of any of paragraphs 67-81, wherein the solid-liquid separation is carried out after preconditioning, but before hydrolysis.

83. The process of any of paragraphs 67-82, wherein the solid fraction resulting from solid-liquid separation, is hydrolyzed and then fermented.

84. The process of any of paragraphs 67-83, wherein the liquid fraction resulting from the solid-liquid separation, is reused as water in fermentation.

85. The process of any of paragraphs 67-84, wherein the solid-liquid separation is carried out after hydrolysis, but before fermentation.

86. The process of any of paragraphs 67-85, wherein the solid fraction resulting from the solid liquid separation, is fermented.

87. The process of any of paragraphs 67-86, wherein the phenol oxidizing enzyme is a laccase.

88. The process of any of paragraphs 67-87, wherein the hemicellulase is selected from a xylanase (e.g., an *Aspergillus aculeatus* or *Aspergillus fumigatus* xylanase), and a xylosidase (e.g., *Aspergillus fumigatus* beta-xylosidase).

89. The process of any of paragraphs 67-88, wherein the cellulosic material is un-detoxified.

90. The process of any of paragraphs 67-89, wherein the cellulosic material is unwashed.

91. The process of any of paragraphs 67-90, wherein the pretreated cellulosic material is dilute acid pretreated cellulosic material.

92. The process of any of paragraphs 67-91, wherein the pretreated cellulosic material is auto-hydrolyzed pretreated cellulosic material.

93. The process of any of paragraphs 67-92, wherein the hydrolysis is carried out at 10-40% TS, such as 15-35% TS, such as 20-30% TS.

94. The process of any of paragraphs 67-93, wherein the cellulosic material is pretreated unwashed corn stover (PCS), corn cob, wheat straw, rice straw and switch grass.

95. The process of any of paragraphs 67-94, wherein the preconditioning occurs at 5-50% TS, such as 10-40% TS, such as 15-35% TS, such as 20-30% TS.

96. The process of any of paragraphs 67-95, wherein the preconditioning occurs for at least 30 minutes, e.g., at least 1 hour, 2, hours, 4 hours, 8 hours, 12 hours, or 24 hours, such as 30 minutes to 24 hours.

97. The process of any of paragraphs 67-96, wherein the preconditioning occurs at a temperature between 20-70° C., such as between 40 and 60° C., such as around 50° C.

98. The process of any of paragraphs 67-97, wherein the phenol oxidizing enzyme, especially laccase, loading is between 1-500 micrograms, such as 5-100 micrograms EP/g cellulose.

99. The process of any of paragraphs 67-98, wherein the hemicellulase loading is between 0.01 and 20 mg EP/cellulose, such as 0.1-1 mg EP/g cellulose.

100. The process of any of paragraphs 67-99, further comprising recovering the fermentation product, e.g., by distillation.

101. The process of any of paragraphs 67-100, wherein the hydrolysis and fermentation are carried out as separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC).

102. The process of any of paragraphs 67-101, wherein the cellulolytic enzyme preparation is of fungal origin.

103. The process of any of paragraphs 67-102, wherein the cellulolytic enzyme preparation is derived from *Trichoderma* (e.g., *Trichoderma reesei*).

104. The process of any of paragraphs 67-103, wherein saccharification is carried out in the presence a cellulolytic enzyme preparation including enzyme activities selected from the group of endoglucanase, cellobiohydrolase, and beta-glucosidase (e.g., *Aspergillus fumigatus* or *Aspergillus oryzae* beta-glucosidase).

105. The process of any of paragraphs 67-104, further wherein saccharification is carried out using a polypeptide having cellulolytic enhancing activity (e.g., a *Thermoascus aurantiacus* or *Penicilluim emersonii* cellulolytic enhancing polypeptide).

106. The process of any of paragraphs 67-105, further wherein saccharification is carried out using one or more enzymes selected from hemicellulase, expansin, esterase, laccase, ligninolytic enzyme, pectinase, peroxidase, protease, and swollenin.

107. The process of any of paragraphs 67-106, wherein the hemicellulase is selected from a xylanase (e.g., an *Aspergillus aculeatus* or *Aspergillus fumigatus* xylanase), and a xylosidase (e.g., *Aspergillus fumigatus* beta-xylosidase).

108. The process of any of paragraphs 67-107, wherein the fermentation product is an alcohol (e.g., ethanol or butanol), an organic acid, a ketone, an amino acid, or a gas.

109. The process of any of paragraphs 67-108, wherein the process results in an increased solid-liquid separation compared to when no phenol oxidizing enzyme and hemicellulase are present or added.

110. The process of any of paragraphs 67-109, wherein the fermentation product is an alcohol (e.g., ethanol or butanol), an organic acid, a ketone, an amino acid, or a gas.

111. A process for producing sugars, comprising:
  (a) preconditioning a pretreated cellulosic material with a phenol oxidizing enzyme and/or a hemicellulase;
  (b) hydrolyzing the pretreated cellulosic material using a cellulolytic enzyme preparation; and
  (c) solid-liquid separation of the pretreated cellulosic material resulting in a solid fraction and a liquid fraction;
  wherein the preconditioning occurs prior to or during hydrolysis and the solid-liquid separation occurs after preconditioning but before hydrolysis, or after hydrolysis.

112. The process of paragraph 111, wherein a phenol oxidizing enzyme is present or added:
  during preconditioning; or
  after preconditioning, but before hydrolysis; or
  during hydrolysis.

113. The process of paragraph 111, wherein a hemicellulase is present or added:
  during preconditioning; or
  after preconditioning, but before hydrolysis; or
  during hydrolysis.

114. The process of paragraph 111, wherein a phenol oxidizing enzyme and a hemicellulase are present or added:
  during preconditioning; or
  after preconditioning, but before hydrolysis; or
  during hydrolysis.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A process of producing a fermentation product from pretreated cellulosic material, comprising the steps of:
   i) preconditioning said pretreated cellulosic material;
   ii) hydrolyzing said cellulosic material of step i) in the presence of a cellulolytic enzyme preparation to produce sugars;
   iii) fermenting said sugars of step ii) in the presence of a microorganism to produce said fermentation product;
   wherein a solid-liquid separation step, resulting in a solid fraction and a liquid fraction, is carried out:
      a) after preconditioning step i), but before hydrolyzing step ii); or
      b) after hydrolyzing step ii), but before fermenting step iii);
   wherein a phenol oxidizing enzyme is present or added:
      during preconditioning step i); or
      after preconditioning step i), but before hydrolyzing step ii); or
      during hydrolyzing step ii);
   wherein a hemicellulase is present or added:
      during preconditioning step i); or
      after preconditioning step i), but before hydrolyzing step ii); or
      during hydrolyzing step ii)
   wherein said solid-liquid separation step is carried out after said cellulosic material is subjected to said phenol oxidizing enzyme and said hemicellulase; and wherein separation into the solid fraction and the liquid fraction is improved as compared to the same process where said phenol oxidizing enzyme and said hemicellulase are not present or added.

2. The process of claim 1, wherein said phenol oxidizing enzyme is a laccase.

3. The process of claim 1, wherein said hemicellulase is selected from the group consisting of a xylanase and a xylosidase.

4. The process of claim 1, wherein said cellulosic material is un-detoxified.

5. The process of claim 1, wherein said cellulosic material is unwashed.

6. The process of claim 1, wherein said solid-liquid separation is carried out after preconditioning step i), but before hydrolyzing step ii).

7. The process of claim 1, wherein said pretreated cellulosic material is dilute acid pretreated cellulosic material.

8. The process of claim 1, wherein said solid fraction resulting from said solid-liquid separation step, is hydrolyzed and then fermented to produce said fermentation product.

9. The process of claim 1, wherein said liquid fraction resulting from said solid-liquid separation step, is fermented to produce said fermentation product.

10. The process of claims 8 or 9, wherein said fermentation product from said solid fraction and/or the liquid fraction fermentation(s) is/are, optionally recovered.

11. The process of claim 1, wherein said liquid fraction is detoxified after said solid-liquid separation to produce a detoxified liquid fraction.

12. The process of claim 11, wherein said detoxified liquid fraction is hydrolyzed together with said solid fraction and then fermented.

13. The process of claim 1, wherein said solid fraction resulting from said solid-liquid separation step, is hydrolyzed and then fermented together with said liquid fraction resulting from said solid-liquid separation step.

14. The process of claim 1, wherein said solid-liquid separation step is carried out after hydrolysis, but before fermentation.

15. The process of claim 1, wherein said pretreated cellulosic material is auto-hydrolyzed pretreated cellulosic material.

16. The process of claim 3, wherein said xylanase is a *Aspergillus aculeatus* xylanase or a *Aspergillus fumigatus* xylanase.

17. The process of claim 3, wherein said xylosidase is a *Aspergillus fumigatus* beta-xylosidase.

* * * * *